Figure 1:
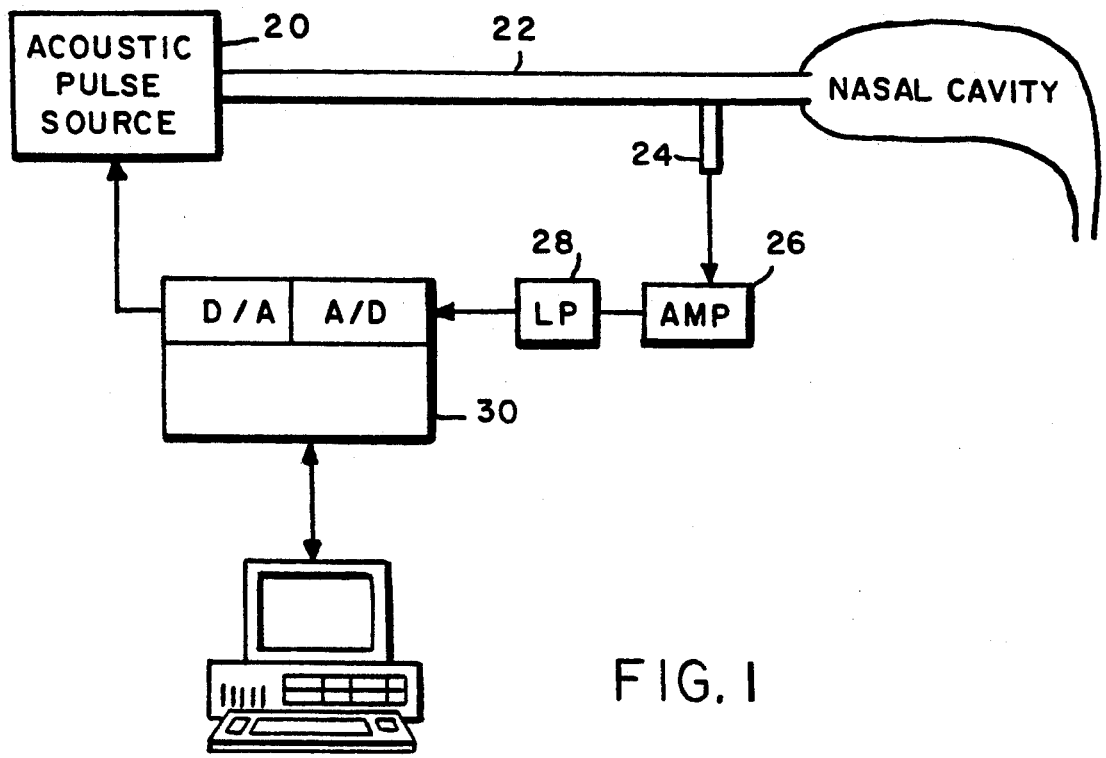

United States Patent [19]
Jackson et al.

[11] Patent Number: 5,316,002
[45] Date of Patent: May 31, 1994

[54] NASOPHARYNGEALOMETRIC APPARATUS AND METHOD

[75] Inventors: Andrew C. Jackson, Brookline; Mark Horenstein, Newton, both of Mass.

[73] Assignee: Trustees of Boston University, Boston, Mass.

[21] Appl. No.: 84,575

[22] Filed: Jun. 29, 1993

[51] Int. Cl.⁵ .............................................. A61B 8/12
[52] U.S. Cl. ............................. 128/602.06; 128/898; 128/660.07
[58] Field of Search ...................... 128/660.01, 660.07, 128/662.06, 720, 898; 73/597; 514/4

[56] References Cited

U.S. PATENT DOCUMENTS

| | | | |
|---|---|---|---|
| 4,326,416 | 4/1982 | Fredberg | 73/597 |
| 5,179,079 | 1/1993 | Hansen et al. | 514/4 |

Primary Examiner—William E. Kamm
Assistant Examiner—George Manuel
Attorney, Agent, or Firm—Lappin & Kusmer

[57] ABSTRACT

This invention relates to an acoustic pulse response system for determining the shape of the nasopharyngeal cavity in a subject by introducing an acoustic impulse through a wave tube into the respective nasal cavities of the subject. The acoustic signals and acoustic reflections thereof with respect to each one of said nasal cavities with both open and closed velums are detected by a microphone located in a wall of the tube, the microphone generating electrical signals proportional to both the impulse and acoustic reflections. The length of the nasal septum is determined, and the value of the area-distance function of the nasopharyngeal cavity is computed from the electrical signals and the length of the nasal septum.

13 Claims, 1 Drawing Sheet

NASOPHARYNGEALOMETRIC APPARATUS AND METHOD

The present invention relates to determination of the shape of nasopharyngeal cavities, and more particularly to the determination of such shape using acoustic, broadspectrum response measurements.

The nasal passage, formed primarily of the nasal cavities and the contiguous nasopharynx, serves as the primary airway for children and adults, and is the obligate air-way in neonates. Because there are clinical conditions that significantly alter the shape of the nasopharynx (e.g., adenoiditis, oral-facial anomalies) a determination of its shape can provide important and clinically useful information. During speech, the production of nasal consonants requires an appropriate acoustic balance between the nasal and oral cavities which can become comprised with velopharyngeal inadequacy. Given the importance of nasal airway obstruction and proper assessment of velopharyngeal function during speech, several methods of evaluating nasal and nasopharyngeal patency have been developed recently including rhinomanometry and nasometry.

Rhinomanometry by measurement of the pressure drop across the nasal cavity and airflow through the nose provides an estimate of resistance as the ratio of pressure divided by flow. This technique, however, is prone to several sources of artifacts, requires some level of patient cooperation and in up to 20% of children studied, reliable data cannot be obtained.

Nasometry involves the measurement of the sound (via microphones) transmitted through each nostril and the oral cavity during phonation. The sound from each nostril, separated by a plate which rests on the upper lip, is compared to the acoustic energy transmitted through the oral cavity and results in a "nasalance" score. It has been shown, however, that there is little correlation between nasalance scores and nasal cross-sectional areas.

A more serious disadvantage of these techniques is that the pressure drop across, and the energy transmitted through the nasal airway is almost entirely dominated by that portion of the passageway where the cross-sectional area is a minimum, i.e., the liminal valve, which is just posterior to the alar rim. Thus, measurements of nasal resistance or nasalance are predominately measures of liminal valve cross-sectional area and are relatively insensitive to the shape of other sections of a nasal cavity or to the shape of the nasopharynx.

A more recently developed technique, acoustic rhinometry, provides a non-invasive estimate of the geometry of the nasal cavity from an acoustic pulse response measurement. This technique does not have the above limitations and has been shown to be able to map the cross-sectional area of the nasal cavity. It is known that it is possible to estimate the shape of a cavity expressed as its cross-sectional area as a function of distance, x, from its inlet. The relationship between the area and distance is called the area-distance function, and is denoted by $A(x)$. $A(x)$ is typically computed using the standard method described in detail by Jackson, A. C., J. P. Butler, E. J. Millet, F. G. Hoppin, Jr., and S. V. Dawson, *Airway geometry by analysis of acoustic pulse response measurements. J. Appl. Physiol.* 43:523-536, 1977(18) and incorporated herein by reference.

The idea of estimating the shape of a cavity from a measurement of its acoustic pulse response was first suggested by Sondhi and Gopinath, *Determination of vocal tract shape from impulse response at the lips, J. Acoust. Soc. Am.* 49:1867-1873, 1971, primarily for use in the oral cavity. Very rapid estimates (e.g. once every 55 ms) of the shape of the cavity, expressed as its $A(x)$, is then computed from the acoustic pulse response (APR) which is determined using a short duration pressure pulse applied to the inlet of the cavity and its reflections from that cavity. The APR technique has since been used by several investigators to measure the $A(x)$ in excised dog lungs, tracheostomized dogs, human oral cavities, human upper airways, human tracheas, and human nasal cavities. Reviews of this method have recently been published in Hoffstein, V. and J. J. Fredberg, *The acoustic reflection technique for non-invasive assessment of upper airway area. Eur. Respir. J.* 4:602-611, 1991; and Marshall I., M. Rogers, and G. Drummond. *Acoustic reflectometry for airway measurements. Principles, limitations, and previous work. Clin. Phys. Physiol. Meas.* 12:131-141, 1991. This method has been shown to provide reasonably accurate estimates of the shape of various portions of the respiratory system including central airways in tracheostomized dogs and in humans, the oral cavity, upper airways, trachea, and the nasal cavity.

There are four fundamental assumptions made in the development of the equations used to compute $A(x)$ from a measure of an acoustic response. These assumptions are that; 1) the waves of the impulse propagate within the cavity as plane waves, 2) there are no parallel pathways, 3) the walls of the cavity are acoustically rigid, and 4) there are negligible viscous acoustic losses. Considering the first assumption, it is possible to estimate from theoretical considerations whether acoustic waves (with a given frequency content) will propagate as plane waves in a cavity of known dimensions. Such waves will propagate in tubes with circular cross-section as plane waves provided that the wave length, $\lambda$, is greater than $1.86\pi$ times the diameter of the tube. Wave length $\lambda$ is, as well known, $c/f$, where c is the wave propagation velocity (34,600 cm/s in room air) and f is frequency. If the diameter of the wave-tube used in these measurements is 1.4 cm, the pressure waves with frequencies below 14.5 kHz will propagate as plane waves. Any portion of the signal that may be propagating in some higher order mode and not as a plane wave, can be eliminated by filtering the signal above 14.5 kHz. Lang, *Clinical anatomy of the nose, nasal cavity and paranasal sinuses.* Georg Thieme Verlag, Stuttgart-New York, 1989. p. 52, gives the maximum transverse dimension of the nasal cavity as 4.57 cm. Thus, in a tube of this diameter with a circular cross-section, only waves with frequencies below about 5 kHz will propagate as plane waves. This prediction is probably quite erroneous with respect to a nasal cavity which typically does not have a circular cross-section. Non-plane wave propagation becomes very noticeable by the existence of rather large high frequency oscillations which result in instabilities in the $A(x)$ computation.

The validity of the second assumption, i.e., that there are no parallel pathways, can be established simply from anatomical considerations. For distances in a nasal cavity from the entrance thereof to the posterior margin of the nasal septum, there are no parallel pathways. Thus, the second assumption is relatively valid for a nasal cavity, and the acoustic response technique would be expected to provide reasonably accurate estimates of its shape. However, once past the posterior margin of the nasal septum, the contralateral nasal cavity and the nasopharynx represent parallel pathways. The second assumption thus is clearly not true for the nasopharynx because where the measurement is made through one nostril, the contralateral nasal cavity represents a parallel pathway with that nostril and the nasopharynx.

The validity of the other two assumptions are much more difficult to determine theoretically but they can be assessed experimentally. It is important to note that even though these assumptions may not be strictly valid, their influence can be considered to be negligible if the technique does in fact return accurate estimates of cross-sectional areas. For example, since the accuracy of acoustic rhinometry has been established for the nasal cavity (Hilberg, O., Jackson, A. C., Swift, D. L., and O. F. Pedersen. *Acoustic rhinometry: Evaluation of nasal cavity geometry by acoustic reflections. J. Appl. Physiol.* 66:295–303, 1989), it can be assumed that even though there may be viscous losses and the wall may not be rigid, these factors have negligible influences on the $A(x)$ estimate. Similar evidence has been provided that this technique accurately estimates the subglottal airways in excised and in-vivo dog lungs, casts of human central air-ways, as well as the supraglottal airways in humans. Thus, even though strict validity of these assumptions has not been demonstrated in these cavities, they are generally accepted as being generally valid.

There has been some question as to the validity of the rigid wall assumption in human subglottal air-ways. To decrease the influence of wall compliance, the prior art has suggested using a gas mixture (80% helium and 20% oxygen) whose density is less, and in which the wave propagation velocity is about twice that in room air. As is well known, because of this greater propagation velocity, significantly higher frequencies can be used before the plane wave propagation assumption becomes invalid. At these higher frequencies, the cavity walls would behave dynamically more rigidly due to their mass, and by including these higher frequencies the influence of wall motion would be reduced.

If the four assumptions listed above are valid, the prior art technique should provide a reasonably accurate estimate of the nasopharyngeal $A(x)$. In such case, the $A(x)$ for distances beyond the posterior septal margin should be identical whether measured from the right or left nostril. Further, $A(x)$ should go to a value of zero when measured with the subject's velum closed. In all subjects, the $A(x)$s determined for distances less than the length of the nasal septum are nearly equal in a given nostril whether the velum is open or closed. However, for distances greater than or beyond the length of the nasal septum, in no subject is the $A(x)$ measured in the right nostril with closed velum ($A_{R,c}(x)$) equal to the $A(x)$ measured in the left nostril with closed velum ($A_{L,c}(x)$), or the $A(x)$ measured in the right nostril with open velum ($A_{R,o}(x)$) equal to the $A(x)$ measured in the left nostril with open velum ($A_{L,o}(x)$). Furthermore, for distances beyond the NSL, the $A_c(x)$ is less than the $A_o(x)$ in both the right and left measurements. However, in no subject does the closed velum $A_c(x)$ go to a value of zero which it should if the viscous losses and the influence of the contralateral nasal cavity were negligible. The conclusion then is that the nasopharyngeal $A(x)$ is not accurately estimated using the prior art technique.

It is therefore clear that it would be desirable to have a non-invasive, acoustic pulse response technique that does provide data related to the shape of the nasopharynx, thus permitting one to evaluate patients with oral-facial anomalies since such individuals frequently manifest significant velopharyngeal impairment. Because as noted, this APR technique can provide very rapid estimates of $A(x)$, it would be applicable to study the dynamics of the nasopharynx during speech. Another useful clinical application of an acoustic nasopharyngealometric technique would be to estimate the degree of obstruction due to adenoiditis, inasmuch as surgeons and patients are becoming increasingly sensitive to adequate quantitative evaluation of the degree of nasopharyngeal obstruction to justify adenoidectomies. As earlier noted, however, because of the failure of one or more of the basic assumptions underlying computation of $A(x)$ to hold true with respect to the combined nasal cavities and nasopharynx, current acoustic rhinometric techniques do not provide accurate estimates of the $A(x)$ for the nasopharyngeal cavity.

A principal object of the present invention is therefore to provide a noninvasive, acoustic, broad-spectrum response system that provides data related to the shape of the nasopharynx. Other objects of the present invention are to provide an acoustic nasopharyngealometric system in which the effects of the contralateral nasal cavity on the accurate determination of $A(x)$ are substantially overcome. Other objects of the present invention will in part be obvious and will in part appear hereinafter.

Generally, the foregoing and other objects are achieved by implementation of methods of compensating for the influence of the parallel nasal cavities in the nasal cavities on the determination of the $A(x)$ of the nasopharyngeal cavity, involving the steps of introducing a broad-spectrum acoustic signal such as an acoustic pulse through a wave tube into a nasopharyngeal cavity; detecting that pulse and acoustic reflections thereof from the nasopharyngeal cavity at a point in the tube between the source of the pulse and the nasopharyngeal cavity; generating electrical signals proportional to both the pulse amplitude and acoustic reflections thereof from the nasopharyngeal cavity; processing the electrical signals, as by amplifying and low-pass filtering to remove frequencies above about 14.5 kHz; determining the length of the nasal septum; and computing the value of $A(x)$ for the nasopharyngeal cavity from the processed signals and the length of the nasal septum.

Apparatus embodying the principles of the present invention generally comprise an acoustic pulse source, a wave tube connectable to a nasal cavity so that an input pulse from the source can be launched into the latter through the tube, microphonic means disposed in the tube adjacent the end thereof couplable to the nasal cavity for generating signals proportional to both the amplitude of the input pulse and acoustic reflections thereof from the nasal and naso-pharyngeal cavities, electronic means for amplifying and low-pass filtering those acoustic reflections, and electronic computer means for determining the $A(x)$ of the nasopharyngeal cavity from the amplified, filtered signals.

The invention accordingly comprises the apparatus possessing the construction, combination of elements and arrangement of parts, and the method comprising the several steps and the relation of one or more of such steps with respect to each of the others, all as exemplified in the following detailed disclosure, and the scope of the application of which will be indicated in the claims.

Figure 2:
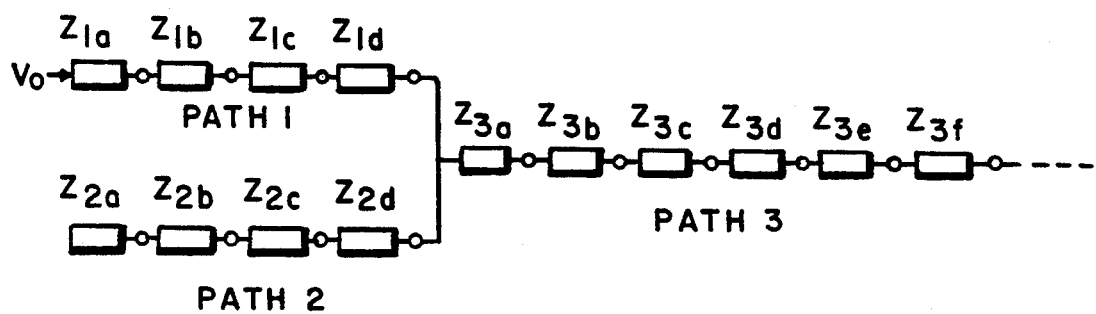

For a fuller understanding of the nature and objects of the present invention, reference should be had to the following detailed description taken in connection with the accompanying drawings in which like numerals in the several drawings are employed to denote like parts, and wherein FIG. 1 is shown in block diagram of acoustic apparatus embodying the principles of the present invention; and FIG. 2 is a block representation of a transmission line analogy of parallel nasal cavities (represented by multi-segmented lines 1 and 2) in series with a nasopharyngeal cavity (represented by multisegmented line 3).

As shown in the drawing, the apparatus of the present invention includes acoustic wave source transducer 20 for producing an acoustic pressure wave, conduit means such as wave tube 22 into one end of which an broad-spectrum acoustic wave from source 20 can be launched. Microphone 24 is provided for detecting the propagation of both the original acoustic waves and reflections thereof in tube 22 at a location between the ends of tube 22, and for generating electrical signals proportional to detected acoustic waves. For processing those electrical signals, the apparatus typically includes electronic amplifier means 26 for amplifying the electrical signals and low-pass filter 28 connected for filtering the electrical signals. Means are provided for determining the length of the nasal septum of the subject in whom the shape of the nasopharyngeal cavity is to be measured. Computation means, typically in the form of electronic computer means 30 are provided for computing A(x) from the length of the nasal septum and the processed electrical signals.

One end of wave tube 22 is typically acoustically coupled to source 20, and microphone 24 is preferably positioned at a point in the wall of tube 22 adjacent the other or distal end of the tube. Signal source transducer 20, the source of a broad spectrum of frequencies, preferably is an electrical spark generator capable of producing broad-spectrum acoustic signals with energy at much higher frequencies that the electromechanical devices typically used in the prior art. Thus, the present invention allows one to determine whether there are differences between nasal A(x) measurements made with room-air (f < 14.5 kHz) and with gas mixtures such as He-Ox at considerably higher frequencies (e.g. f < 29 kHz).

The method of the present invention requires initial determination of where the nasal cavity ends and the nasopharynx begins in each subject. To this end, in one embodiment, the distance to the posterior margin of the nasal septum, i.e. the nasal septum length (NSL), is invasively determined using a flexible nasopharyngofiberscope (Pentax, model PNE) that is passed into one nasal cavity of a subject and visual determination is made when the instrument tip reaches the end of the nasal septum. The nasopharyngo-fiberscope is marked at the margin of the nostril, withdrawn and the distance that it had been inserted is measured, and the measurement used as the NSL. As will be seen hereinafter, in another embodiment of the present invention, the NSL is determined non-invasively from analysis of the A(x)'s.

The distal end of wave tube 22 is inserted into a nostril of the subject, making certain that the tube is well seated so that the juncture between the end of the nostril and tube presents no acoustic discontinuity. In one embodiment, the exterior cross-sectional configuration of at least the distal end of wave tube 22 is ellipsoidal (which term is to be construed herein to include ovals as well as ellipses) to match more closely the cross section configuration of human nostrils and thus, when properly dimensioned for the subject, minimizing distortion of the nostril when inserted into the latter. A circular internal cross-section configuration of tube 22 is preferably provided regardless of the external configuration.

Source 20 is then activated to generate an acoustic signal that travels down the tube and into the nasal cavity. Signals proportional to pressure of both incident and reflected waves are generated by microphone 24, preferably then digitized, stored in computer 26 which then computes the A(x) using the standard method described in detail by Jackson, A. C., J. P. Butler, E. J. Millet, F. G. Hoppin, Jr., and S. V. Dawson, *Airway geometry by analysis of acoustic pulse response measurements. J. Appl. Physiol.* 43:523–536, 1977(18) and incorporated herein by reference. A(x) is measured from the resulting electrical signals derived from the acoustic waves detected for at least one nasal cavity, but preferably for both the right and left nasal cavities while the subject maintains his or her velum in both the open and closed position. Measurement can be taken alternately between the nostrils or alternatively, simultaneously in both nostrils. In the former case, it is preferred to minimize the distortion of the nostril by introduction of the wave tube. In the latter case, some distortion is acceptable provided that the distortion is substantially the same degree in each nostril.

The method of the present invention accounts for the two parallel pathways of the nasal cavities, relying on knowledge of the nasal septum length which can be obtained, as noted above, by invasive methods. It has now been found that the NSL can also be determined by determining A(x) for both nostrils with velum closed and open. From those A(x) it is seen that at or near the junction of the nasal and nasopharyngeal cavities, there is a large and rapid increase in the A(x) in normal subjects whether measured in the right or left nostril. Significantly, it has also now been found that A(x)s for the open and closed velum diverge consistently and significantly from zero at the anatomical point where the hard palate ends and the soft palate begins, i.e. in close proximity to the posterior margin of the nasal septum.

Measurements of the broad-spectrum acoustic pulse response are preferably made in both the right and left nostrils of each subject with conditions of open and closed velums. To close the velum, the subject is instructed to breath through pursed lips and not allow any air to pass through the nose. To maintain the velum in the open position, the subject is instructed to breath through the nose with the mouth closed. One can determine whether the subject is capable of maintaining a closed velum by monitoring the temperature of the air in the alar rim with thermocouples. It has been found that with a closed velum, the temperature does not vary with the respiratory cycle but remains constant and close to room temperature. With an open velum, the temperature varies with the respiratory cycle, increasing with expiration and decreasing with inspiration. Prior to making the measurements, it is preferred to administer oxymatazolene aerosol to each nostril to maximally dilate each nostril and thus reduce the reported time dependent variations in nasal geometry. From these, the AR(x) and AL(X) are computed with the modifications outlined hereinafter, and compared. For distances appropriate for the nasopharynx (i.e., for x>NSL as determined from direct measurements with a nasopharyngo- scope), the AR(x) and AL(X) should be equal and they both should go to zero at an appropriate distance with the closed velum.

The preferred method for accounting for the effects of the contralateral nasal cavity can be advantageously described employing an electrical analogy to analyze transmissions and reflections in the bifurcated airway, inasmuch as acoustic and electromagnetic plane waves obey similar wave equations and hence share similar properties. Acoustic waves in a hollow tube represent variations in pressure p(x) and longitudinal velocity u(x) that satisfy the differential equations $$-\delta p/\delta x = \rho_o(\delta u/\delta t) \quad (1)$$

and $$-\rho_o \gamma P_o(\delta u/\delta x) = \delta p/\delta t \quad (2)$$

where
$\rho_o$ is the ambient air density,
$P_o$ is the equilibrium gas pressure, and
$\gamma$ is the ratio of specific heat of the transmission medium at constant gas pressure to the specific heat at constant gas volume.

These two equations can be combined to yield the classic acoustic wave equation $$\delta^2 p/\delta x^2 = (\rho_o/\gamma P_o)(\delta^2 p/\delta t^2) \quad (3)$$

where the wave propagation velocity $c_a$ is given by $$c_a = (\gamma P_o/\rho_o)^{\frac{1}{2}} \quad (4)$$

If the wave equation (3) is solved (assuming negligible viscous losses) in the geometry of a closed, rigid walled tube, the tube's characteristic acoustic impedance, $Z_a(x)$, defined by the ratio p(x)/u(x) at any point, becomes $$Z_a(x) = \rho_o c_a/A(x) \quad (5)$$

where A(x) is the cross-sectional area of the tube at position x (i.e., the area-distance function). It is this equation that allows us to compute A(x) from a measure of the acoustic pulse response (APR), and it is here that the conditions of plane wave propagation, no parallel pathways, negligible viscous losses, and rigid walls are assumed.

Transverse electromagnetic (TEM) waves propagating along a two-wire transmission line, if expressed in the form of transverse voltage and longitudinal current, obey a similar set of equations that describe the electromagnetic induction and displacement-current effects. Specifically, the voltage V(x) and current I(x) are related by $$-\delta I/\delta x = C(\delta V/\delta t) \quad (6)$$

and $$-\delta V/\delta x = L(\delta I/\delta t) \quad (7)$$

where L and C are the inductance and capacitance per unit line length, respectively.

These equations are direct extensions of Maxwell's electromagnetic equations. As in the acoustic case, equations (6) and (7) can be combined into a single second-order differential wave equation $$\delta^2 V/\delta x^2 = LC(\delta^2 V/\delta t^2) \quad (8)$$

where the propagation velocity c is given by $$c = 1/(LC)^{\frac{1}{2}} \quad (9)$$

and the line impedance by $$Z_e = \sqrt{L/C} \quad (10)$$

The acoustic and electrical wave equations (4) and (8), identical in mathematical form, predict propagation of waves at constant velocity. The propagating waves need not be sinusoidal, but can take the form of transients of arbitrary shape, including step or impulse functions. Acoustic and electromagnetic waves can be made analogous by equating pressure p(x) with voltage V(x) and velocity u(x) with current I(x). Any reflections or transmissions that occur at the discontinuities of an acoustic airway system can thus be predicted or analyzed by the analogous events in an equivalent electrical transmission line system.

The reflection from a voltage pulse of amplitude $V_1^+$ incident from a line of impedance $Z_1$ onto a line of impedance $Z_2$ is given by the expression $$V_1^- = V_1^+ (Z_2 - Z_1)/(Z_2 + Z_1) = R_{12} V_1^+ \quad (11)$$

where the superscript (+) denotes a positive traveling wave, the (−) superscript denotes a negative traveling wave, and the factor $R_{12}$ designates the reflection coefficient. Similarly, the amplitude of the pulse transmitted from line 1 onto line 2 can be expressed by $$V_2^+ = V_1^+ (2Z_2)/(Z_2 + Z_1) = T_{21} V_1^+ \quad (12)$$

where $T_{21}$ is the transmission coefficient.

The reflection and transmission coefficients described above are also valid in the acoustic domain and form the basis for present methods used to determine the area-distance function of a single hollow airway. These known methods involves measuring the reflections that occur when a pulse in pressure is applied at the airway entrance. The subsequent reflections are sampled at discrete intervals, allowing the airway to be modeled as a sequence of short tube increments of varying cross-sectional area. The segmental representation of transmission lines is discussed in more detail hereinafter. The incremental length of the equivalent segments is determined by the sampling interval and by the wave propagation velocity. From the measured acoustic pulse response (APR), the characteristic impedance, $Z_a(x)$ as a function of distance is computed. Finally, the area-distance function, A(x), is computed using equation (5).

As is known, computation of the transmitted pulse amplitudes in a transmission line system can be made using a Thevenin equivalence model for describing the interaction of an incoming pulse with an impedance discontinuity. Assume that a voltage pulse, or by analogy, an acoustic pressure pulse, of amplitude V+ is incident from a line of impedance $Z_1$ onto a second line of impedance $Z_2$. At the moment of impact, before the occurrence of any further reflections from downstream of the impedance discontinuity, the effect of the second line on the first can be modeled as a load resistance of value $Z_2$. Application of appropriate boundary conditions, in this case that the voltage and current both be continuous across the interface, yields the respective equations $$V_1^- + V_1^+ = V_2^+ \quad (13)$$

and $$(V_1^- - V_1^+)/Z_1 = V_2^+/Z_2 \quad (14)$$

In these latter equations, the net line voltage on either side of the boundary consists of the sum of the positive traveling wave amplitude $V^+$ and the negative traveling wave amplitude $V^-$. Similarly, the net line current on either side consists of the difference between $V^+$ and $V^-$ divided by the line impedance. Note that $V^-$ equals zero on line 2 because any reflections that might later arrive from downstream of the discontinuity do not effect events at the initial moment of impact of the $V_1^+$ pulse on the discontinuity. The above boundary conditions can be solved for the transmitted pulse amplitude $V_2^+$ associated with the event, yielding $$V_2^+ = 2V_1^+ [(Z_2)/(Z_2 + Z_1)] \quad (15)$$

This latter equation is identical to equation (12) and describes the amplitude of the voltage pulse transmitted onto line 2 from line 1. The reflected pulse amplitude predicted by these boundary conditions becomes $$V_1^- = V_1^+ [(Z_2 - Z_1)/(Z_2 + Z_1)] \quad (16)$$

which describes the usual coefficient of the pulse reflected back onto line 1 as given by equation (11). The voltage division implied by equation (15) suggests that the transmitted pulse magnitude can also be determined from a simple Thevenin equivalent circuit. The transmitted pulse amplitude $V_2^+$ becomes equivalent to the voltage measured across $Z_2$ as determined by simple voltage division.

A similar model can also be applied to the case where the incident line, one of two parallel lines with impedances $Z_1$ and $Z_2$ (representing the parallel nasal cavities) feeds a third line having impedance $Z_3$ (representing the pharyngeal cavity) in series with the first two as shown in FIG. 2. In this latter case, the Thevenin equivalent circuit would show a parallel combination of line impedances $Z_2$ and $Z_3$ (denoted with the character $||$), forming the load to impedance $Z_1$ so that the magnitude of the pulses transmitted respectively onto lines $Z^2$ and $Z_3$ become $$V_2^+ = V_3^+ = 2V_1^+ [(Z_2 || Z_3)/(Z_2 || Z_3 + Z_1)] \quad (17)$$

The voltage pulses transmitted onto lines 2 and 3 have the same magnitudes because the lines are connected in parallel. If lines 2 and 3 have different impedances, the transmitted currents will have different magnitudes.

This latter model also suggests that the magnitude of the pulse reflected back onto line 1 can be computed from $$V_1^- = V_1^+ [(Z_2 || Z_3 - Z_1)/(Z_2 || Z_3 + Z_1)] \quad (18)$$

where the parallel combination of $Z_2$ and $Z_3$ has been included in the reflection coefficient. The above sequence of equations can be inverted to provide the value of $Z_3$ from the measured value of $V_1^-$ if $Z_1$ and $Z_2$ are known.

If impedance discontinuities exist downstream of lines 2 and 3, pulses will be reflected back toward the bifurcation point. The subsequent transmission and reflection of these pulses can also be computed using a Thevenin model similar to that described. In this case the magnitude of the pulse transmitted onto lines 1 and 2 by a pulse of amplitude $V_3^-$ arriving from line 3, for example, can be computed from $$V_2^- = V_1^- = 2V_3^- [Z_1 || Z_2/(Z_1 || Z_2 + Z_3)] \quad (19)$$

where the load seen by negative-traveling waves on line 3 consists of the parallel combination of lines 1 and 2. Similarly, the magnitude of the pulse further reflected back onto line 3 will be given by $$V_3^+ = V_3^- [(Z_1 || Z_2 - Z_3)/(Z_1 || Z_2 + Z_3) \quad (20)$$

The method has thus been extended to provide information about impedance changes in line 3 downstream of the bifurcation point.

The most general case consists of a combination of multisegmented, bifurcated lines as shown schematically in FIG. 2 wherein paths 1 and 2 represent two nasal passages with varying area-distance functions $A_1(x)$ and $A_2(x)$, and path 3 represents the nasopharynx with area distance function $A_3(X)$. When an impulse of magnitude $V_0$ is launched at the open end of path 1, representing one of the nostrils, the Thevenin transmission algorithm, when used recursively, predicts the subsequent reflected pulse amplitudes observed at the excitation point. Conversely, inversion of the basic algorithm permits determination of the various segment impedances from the values of the pulse reflections obtained by measurements at the excitation point. Though algebraically intensive, the method is not complicated and is easily performed on a general purpose computer as a post-measurement procedure.

The use of the Thevenin transmission algorithm to determine the impedance distribution of a bifurcated airway can be demonstrated by simulating the system of FIG. 2 electrically using the industry standard SPICE (Simulation Program with Integrated-Circuit Emphasis) software program. These simulations provide impulse response data, $APR_1$ and $APR_2$, arising from application of an impulse into path 1 and into path 2, respectively. The initial reflections of $APR_1$ coming from segments $Z_{1a}$ through $Z_{1d}$ were used to compute the impedances of the segments in path 1. Similarly, the initial reflections of $APR_2$ coming from segments $Z_{2a}$ through $Z_{2d}$ were used to compute the impedances of the segments in path 2. Knowledge of the impedances in paths 1 and 2 along with the remaining reflections of $APR_1$ or $APR_2$ permitted computation of the segment impedances in path 3. In this way one can test the ability of the program written to implement the inverse algorithm to reconstruct the profile of impedances along each line. For these simulations, the segment impedances are chosen to vary arbitrarily. In order to simplify and speed up the calculations, the change in impedance between any two adjacent segments is made small (as they are in the nasal and nasopharyngeal cavities), so that all transmission coefficients have values close to unity and all reflection coefficients have magnitudes of order $\epsilon$, where $\epsilon << 1$. This simplification allows all but primary reflections to be neglected at each line junction, because the observed effects of second and higher order reflections can be shown to be of order $\epsilon^3$ or smaller. The impedance change cannot generally be considered small at the bifurcation point, of course. Hence reflections of order two or higher that occuring at the bifurcating junction must generally be included in the inverse algorithm. Note that the assumption of small impedance changes between segments is not a requirement of the Thevenin transmission model and can be relaxed to accommodate systems with large discontinuities in impedance along a given path.

Accuracy can be improved when higher order reflections are included in the computations which is in agreement with results reported by Marshall I. *Impedance reconstruction methods for pulse reflectometry, Acustica.* 76:118-128, 1992.

The present invention then includes a method of computing the area-distance function of the nasopharyngeal cavity including a modification that accounts for the parallel impedances of the two nasal cavities. This method relies on the separate determination of APR from both the right and left nasal cavities, and knowledge of the NSL. Measurements of the APR from the right and left nostril are made, and from these, the AR(X) and AL(X) are computed using the standard method. The NSL is identified and for distances <NSL in centimeters (that is, for times less than t=NSL/34,600) the AR(X) and AL(X) will be used as the correct values for the right and left nasal cavity cross-sectional areas. Because the cross-sectional areas of the nasopharynx are incorrectly estimated using this technique, the modified technique is used to compute more correct values for the cross-sectional area of the nasopharynx (i.e., for distances >NSL).

While the present invention has been described as using acoustic pulses, the principles of the present invention can be implemented even more advantageously, in some respects, by a different technique employing continuous wideband noise as the input signal. In such case, acoustic wave source transducer 20 is selected for producing a continuous wideband acoustic pressure wave, typically white noise. Current devices for measuring the area-distance function of bodily cavities, exemplified by U.S. Pat. No. 4,326,416, based on the use of transient pressure waves such as acoustic pulses, require a time-separation of the excitation signal and the reflected pressure wave. Such separation necessitates the use of wave tubes 22, typically of 5 meters or more, that are quite unacceptable clinically. By using continuous wideband pressure waves, one can transmit and receive the respective input signals and reflections using a much shorter tube 22, e.g. 580 mm. Further, the use of acoustic transient signals exposes the system to the effects of external acoustic noise of any nature that will interfere with the signal measured and introduce errors into the area-distance function computed.

It will be appreciated that using continuous wideband noise as the input signal eliminates the necessity of time-separating input and reflected signals. The input and reflected signals are superimposed in the acoustic system and the superimposed signals are preprocessed statistically to transform them into pseudo-time space to provide time separation, to eliminate the influence of external noise and to adapt the wideband noise generator to the characteristics of the cavity being examined. The use of an appropriate algorithm to further process the preprocessed signals then provides the desired area-distance function. Apparatus providing the requisite wideband signal generator and the appropriate algorithms for statistical processing are commercially available from SRE Electronics ApS, Lynge, Denmark.

Since certain other changes may be made in the present invention without departing from the scope of the invention herein involved, it is intended that all matter contained in the above description be construed in an illustrative and not in a limiting sense.

What is claimed is:

1. A method of determining the shape of the nasopharyngeal cavity in a subject using acoustic, broad-spectrum response measurements, said method comprising the steps of:
   introducing acoustic signals through conduit means into the input ends of the respective nasal cavities of said subject;
   detecting said acoustic signals and acoustic reflections thereof with respect to each one of said nasal cavities at a point in said conduit means;
   generating electrical signals proportional to the amplitudes of both said acoustic signals and acoustic reflections thereof;
   determining the length of the nasal septum separating said nasal cavities; and
   computing the value of the area-distance function of said nasopharyngeal cavity from said electrical signals and said length of the nasal septum.

2. A method as set forth in claim 1 including the step of successively introducing said acoustic signals into each said nasal cavity.

3. A method as set forth in claim 1 including the step of simultaneously introducing said acoustic signals into both said nasal cavities.

4. A method as set forth in claim 1 wherein said step of determining the length of the nasal septum is effected invasively.

5. A method as set forth in claim 4 wherein said step of determining the length of said septum includes introducing a nasopharyngoscope into at least one of said nasal cavities so as to visually determine the location of the end of the nasal septum.

6. A method as set forth in claim 1 wherein said step of determining the length of the nasal septum is effected non-invasively.

7. A method as set forth in claim 6 wherein said step of determining the length of the nasal septum includes the steps of
   determining the area-distance function of at least one of said nasal cavitities with a closed velum;
   determining the area-distance function of said at least one of said nasal cavities with open velum;
   determining said length of nasal septum in accordance with the distance at which the value of said area-distance functions diverge from zero.

8. A method as set forth in claim 1 including the step of filtering from said electrical signals frequencies above about 14.5 KHz.

9. Apparatus for determining the shape of the nasopharyngeal cavity in a subject using acoustical energy propagated through a conduit acoustically coupled into said cavity through at least one nasal cavity, said apparatus comprising, in combination
   means for introducing acoustical signals into said conduit for propagation therethrough;
   means for measuring the length of the nasal septum of said subject; and
   means for determining the area-distance functions of said cavities in accordance with the propagation of said acoustical signals and reflections thereof and said length of said nasal septum.

10. Apparatus as defined in claim 9 wherein said conduit is dimensioned at least at one end thereof to acoustically couple to a nostril of said subject by insertion therein without substantially distorting said nostril.

11. Apparatus as defined in claim 9 wherein said means for determining include means for detecting said acoustic signals and acoustic reflections thereof with respect to each one of said nasal cavities at a point in said conduit means;

means for generating electrical signals proportional to the amplitudes of both said acoustic signals and acoustic reflections thereof; and means for computing the value of the area-distance function of said nasopharyngeal cavity from said electrical signals for both of said nasal cavities and said length of said nasal septum.

12. Apparatus as defined in claim 9 wherein said conduit is an elongated tube having a substantially circular-cross section configuration internally and a substantially ellipsoidal cross-section configuration externally.

13. Apparatus for determining the shape of the nasopharyngeal cavity in a subject using acoustical energy propagated through a conduit acoustically coupled into said cavity through at least one nasal cavity, said apparatus including means for generating said acoustical energy, and means for measuring the area-distance functions of said cavities in accordance with the propagation of said energy into said cavity and reflections thereof, wherein said conduit is an elongated tube having a substantially circular-cross section configuration internally and a substantially ellipsoidal cross-section configuration externally.

* * * * *